(12) United States Patent
Nagao et al.

(10) Patent No.: US 7,534,912 B2
(45) Date of Patent: May 19, 2009

(54) PROCESS FOR PRODUCING PYROMELLITIC ACID

(75) Inventors: Shinichi Nagao, Kurashiki (JP); Hiroshi Ogawa, Kurashiki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 372 days.

(21) Appl. No.: 10/965,770

(22) Filed: Oct. 18, 2004

(65) Prior Publication Data

US 2005/0085663 A1    Apr. 21, 2005

(30) Foreign Application Priority Data

Oct. 20, 2003    (JP) .............................. 2003-359408

(51) Int. Cl.
*C07C 61/00*    (2006.01)
*C07C 51/16*    (2006.01)

(52) U.S. Cl. ..................... 562/421; 562/400; 562/407; 562/413

(58) Field of Classification Search ................. 562/400, 562/413, 486, 407, 421
See application file for complete search history.

(56) References Cited

U.S. PATENT DOCUMENTS

| 3,852,342 | A |   | 12/1974 | Hanotier |         |
|-----------|---|---|---------|----------|---------|
| 4,755,622 | A |   | 7/1988  | Schammel et al. | |
| 5,041,633 | A | * | 8/1991  | Partenheimer et al. | 562/413 |
| 6,579,990 | B2| * | 6/2003  | Tanaka et al. | 549/239 |

FOREIGN PATENT DOCUMENTS

| JP | 57-38745 A    | 3/1982  |
| JP | 61 027942 A   | 2/1986  |
| JP | 2-184652 A    | 7/1990  |
| JP | 7-116097 B2   | 12/1995 |

\* cited by examiner

*Primary Examiner*—Taylor Victor Oh
(74) *Attorney, Agent, or Firm*—Sughrue Mion, PLLC

(57) ABSTRACT

A process for producing pyromellitic acid which comprises step A for oxidizing durene, thereby obtaining a reaction mixture comprising trimethyl benzoic acid, trimethyl benzyl alcohol and trimethyl benzaldehyde, step B for separating trimethyl benzoic acid, trimethyl benzaldehyde and trimethyl benzyl alcohol from the reaction mixture obtained in step A, and step C for oxidizing trimethyl benzoic acid and/or trimethyl benzaldehyde separated in step B, thereby obtaining pyromellitic acid.

22 Claims, No Drawings

PROCESS FOR PRODUCING PYROMELLITIC ACID

BACKGROUND OF THE INVENTION

1) Field of the Invention

The present invention relates to a process for producing pyromellitic acid by liquid phase oxidation of durene and oxidation derivatives thereof, and specifically to a process for producing pyromellitic acid which comprises oxidizing durene as a starting material in a liquid phase and producing intermediate products step by step and oxidizing thereof, thereby producing pyromellitic acid of a final product in a high yield.

2) Prior Art

Terephthalic acid has been industrially produced in many states by air oxidation of p-xylene in acetic acid solvent in the presence of a bromine-transition metal catalyst. In a liquid phase oxidation reaction employing aromatic hydrocarbons as starting material, it is indispensable to use acetic acid as a solvent in order to obtain aromatic polycarboxylic acids. When acetic acid is used as such solvent, loss of acetic acid occurs by its combustion.

Durene is oxidized with air in the presence of a heavy metal catalyst in the same manner as other alkyl aromatic compounds, whereby pyromellitic acid is produced. However, it is known that pyromellitic acid thus produced forms a complex with a heavy metal(s) due to ortho structure of two carboxylic groups in pyromellitic acid to cause deactivation of the catalyst, so that its yield is lower than that in other alkyl aromatic compounds having no such structure.

As a conventional process for producing pyromellitic acid, Japanese Patent Kokai (Laid-open) No. 57-38745 discloses a process for producing pyromellitic acid which comprises oxidizing polyalkyl aromatic aldehyde in acetic acid solvent in the presence of a cobalt/manganese/bromine catalyst.

Further, Japanese Patent Kokai (Laid-open) No. 2-184652 discloses a process for producing pyromellitic acid which comprises oxidizing durene in a liquid phase in the presence of a cobalt/manganese/bromine catalyst, wherein the catalyst is added in two stages and the reaction is performed in batch wise.

Japanese Patent Publication No. 7-116097 discloses a process for producing pyromellitic acid which comprises oxidizing polyalkyl-substituted aromatic aldehyde or oxidation derivative thereof in water solvent with molecular oxygen in the presence of an iron/manganese/bromine catalyst.

In the production of pyromellitic acid by oxidation of durene, loss of acetic acid as a solvent occurs by its combustion. Thus, a process for producing pyromellitic acid without using acetic acid has been required.

The case where oxidation reaction is performed in water solvent has the defect that polyalkyl-substituted aromatic aldehyde as a raw material for oxidation is high-priced. Further, there are some problems that when oxidation is performed in acetic acid solvent, it is avoidable to apply batch wise.

SUMMARY OF THE INVENTION

An object of the present invention is to provide a process for producing continuously and industrially pyromellitic acid in a high yield by liquid phase oxidation of low-priced durene as a starting material without using acetic acid as a solvent.

As a result of extensive studies to solve the prior art problems, the inventors have found that pyromellitic acid can be obtained continuously in a high yield by oxidizing durene as a starting material step by step under specific procedures and have accomplished the present invention.

That is, the present invention provides a process for producing pyromellitic acid which comprises:

step A for oxidizing durene, thereby obtaining a reaction mixture comprising trimethyl benzoic acid, trimethyl benzyl alcohol and trimethyl benzaldehyde, step B for separating trimethyl benzoic acid, trimethyl benzaldehyde and trimethyl benzyl alcohol from the reaction mixture obtained in step A, and step C for oxidizing trimethyl benzoic acid and/or trimethyl benzaldehyde separated in step B, thereby obtaining pyromellitic acid.

According to the process of the present invention, intended pyromellitic acid is obtained in a high yield by oxidizing durene as a starting material in a liquid phase. The present invention is industrially very significant because the process of the present invention comprising continuous liquid phase oxidation of low-priced durene is industrially very valuable.

DETAILED DESCRIPTION OF THE INVENTION

The present invention will be described in detail below.

(Step A)

Durene of a starting material for oxidation to be used in the present invention is present in a $C_{10}$ distillate of catalytic reforming oils or thermal cracking oils and commercial products thereof separated by distillation can be used. The starting material for oxidation may contain 2,4,5-trimethyl benzaldehyde and 2,4,5-trimethyl benzoic acid which are intermediate products of durene.

In step A, durene is subjected to liquid phase oxidation with molecular oxygen, whereby a reaction mixture comprising trimethyl benzoic acid, trimethyl benzyl alcohol and trimethyl benzaldehyde is obtained. Herein, trimethyl benzoic acid, trimethyl benzyl alcohol and trimethyl benzaldehyde represents 2,4,5-trimethyl benzoic acid, 2,4,5-trimethyl benzyl alcohol and 2,4,5-trimethyl benzaldehyde, respectively as long as they are particularly not designated.

In the oxidation reaction of step A, it is preferable to use a solvent. Water is preferable as the solvent. The weight ratio (SR) of the solvent to durene is preferably in the range of 0.2 to 10 and more preferably in the range of 1 to 5. Further, it is preferable that trimethyl benzoic acid is present together with durene of a starting material in the reaction system. In this case, it is preferable that an amount of trimethyl benzoic acid is in the range of 0.1 to 40% by weight to total amount of the solvent. Herein, new trimethyl benzoic acid may be fed or trimethyl benzoic acid separated in step B to be described later may be circulated and used. When trimethyl benzoic acid is present together with durene in water as the solvent, the selectivity to trimethyl benzaldehyde and trimethyl benzoic acid as intended products in step A is remarkably improved.

In the oxidation reaction of step A, it is preferable to use a catalyst. At least one species of heavy metal compound is preferable as the catalyst. Herein, as the heavy metal, cobalt, manganese, iron, zirconium and cerium are used, among which cobalt and/or manganese is (are) preferable. These metals can be used as compounds such as organic acid salts and halogenides. It is preferable to use acetic acid salts thereof. The amount of the catalyst to be used is in the range of 0.01 to 2% by weight and preferably in the range of 0.05 to 1% by weight as metal atom to durene as a starting material.

The reaction temperature of liquid phase oxidation in step A is in the range of 90 to 230° C. and preferably in the range of 140 to 200° C. The reaction pressure is in the range of 0.1 to 4.0 MPaG, preferably in the range of 0.2 to 3.2 MPaG and more preferably in the range of 0.4 to 2.5 MPaG.

Pyromellitic acid can be produced by liquid phase oxidation of the reaction mixture obtained in step A as a raw material. However, when trimethyl benzyl alcohol produced in step A and unreacted durene are present in the raw material, the yield of pyromellitic acid becomes low. Therefore, in the present invention, it is preferable to produce pyromellitic acid via the following step B and it is more preferable to produce it via further the following step D or E.

(Step B)

In step B, trimethyl benzoic acid, trimethyl benzaldehyde and trimethyl benzyl alcohol are separated from the reaction mixture obtained in step A. The reaction mixture contains mainly unreacted durene, trimethyl benzoic acid, trimethyl benzaldehyde and trimethyl benzyl alcohol and, when a solvent and a catalyst are used, it further contains water and catalyst components. The process for separating trimethyl benzoic acid, trimethyl benzaldehyde and trimethyl benzyl alcohol from the reaction mixture is not limited. For example, the reaction mixture is separated into each of an oily phase containing mainly unreacted durene, trimethyl benzoic acid, trimethyl benzaldehyde and trimethyl benzyl alcohol and an aqueous phase. Then, the oily phase thus separated is subjected to vacuum distillation, whereby each distillate comprising each of durene, trimethyl benzoic acid, trimethyl benzaldehyde and trimethyl benzyl alcohol as main component is obtained. Trimethyl benzoic acid and trimethyl benzaldehyde thus separated are oxidized in the following step C and converted to pyromellitic acid. Components other than the main components may be contained in the above-mentioned each distillate. However, it is preferable that durene or trimethyl benzyl alcohol is not contained in trimethyl benzoic acid or trimethyl benzaldehyde to be fed to step C. When they are contained, they sometimes exert bad influence on the reaction in step C.

On the other hand, trimethyl benzyl alcohol separated in step B is subjected to oxidation in the following step D or to hydrogenation reduction in the following step E. The reaction products thus obtained by oxidation or the reaction products thus obtained by hydrogenation reduction are fed to step C via step B or step A and effectively converted to pyromellitic acid. Thus, according to the process of the present invention, pyromellitic acid can be produced in a high yield without suffering any influence of trimethyl benzyl alcohol. Further, durene separated in step B can be reused as the starting material in step A or as the solvent in step D.

(Step C)

In step C, trimethyl benzoic acid and/or trimethyl benzaldehyde is (are) subjected to liquid phase oxidation with molecular oxygen, whereby pyromellitic acid is obtained. In the oxidation reaction of step C, it is preferable to use a solvent. Water and/or aliphatic carboxylic acid is (are) preferable as the solvent, among which water is more preferable. The weight ratio of solvent to raw material for oxidation is in the range of 0.2/1 to 10/1 and preferably in the range of 1/1 to 5/1.

In the oxidation reaction of step C, it is preferable to use a catalyst. At least one species of heavy metal compound is preferable as the catalyst. Herein, cobalt, manganese, iron, zirconium and cerium are used as the heavy metal, among which at least one metal selected from the group consisting of cobalt, manganese and iron is (are) preferable. These metals are used as compounds such as organic acid salts and halogenides. It is more preferable to use acetic acid salts and bromides thereof.

Further, it is the most preferable to use a bromine compound(s) as the catalyst. Examples of the bromine compound include inorganic bromides such as hydrogen bromide, sodium bromide, cobalt bromide and manganese bromide and organic bromides such as tetrabromoethane, among which hydrogen bromide, cobalt bromide and manganese bromide are preferable.

The amount of the catalyst is in the range of 0.01 to 1% by weight and preferably in the range of 0.05 to 0.8% by weight as total metal atom to the solvent. Total bromine concentration in the reaction system is in the range of 0.1 to 4.0% by weight and preferably 0.5 to 2.5% by weight as bromine atom to the solvent.

In step C, the reaction temperature of liquid phase oxidation is in the range of 160 to 260° C. and preferably in the range of 180 to 240° C. The reaction pressure is in the range of 0.5 to 5.0 MPaG and preferably in the range of 1.0 to 3.6 MPaG.

Pyromellitic acid is obtained in a high yield by separating the solvent, etc., from the reaction solution of step C.

(Step D)

In step D, trimethyl benzyl alcohol separated in step B is subjected to liquid phase oxidation with molecular oxygen, whereby a reaction mixture comprising trimethyl benzoic acid and trimethyl benzaldehyde is obtained and recycled to step B. In the oxidation reaction of trimethyl benzyl alcohol, it is preferable to use a solvent. The solvent to be used is aromatic hydrocarbons and/or water, preferably durene and/or water and more preferably durene. The amount of the solvent is in the range of 1 to 12 and preferably in the range of 2 to 6 as a weight ratio (SR) of solvent to the raw material for oxidation (trimethyl benzyl alcohol). When durene and/or water is (are) used as the solvent, it is preferable since additional separation step is not necessary in feeding of the reaction mixture obtained in step D to step B. Further, when durene is contained in the reaction system of step D, it is preferable since the selectivity to trimethyl benzaldehyde and trimethyl benzoic acid as intended products of step D is improved.

In the oxidation reaction of step D, it is preferable to use a catalyst. At least one species of heavy metal compound is preferable as the catalyst. Herein, as the heavy metal, cobalt, manganese, copper iron, zirconium and cerium are used, among which it is more preferable to use at least one metal selected from the group consisting of cobalt, manganese and copper. These metals are used as compounds such as organic acid salts and halogenides. It is preferable to use organic acid salts such as acetic acid salts and naphthenic acid salts thereof.

The amount of the catalyst to be used is in the range of 0.01 to 1% by weight and preferably in the range of 0.02 to 0.5% by weight as metal atom to trimethy benzyl alcohol as a raw material for oxidation.

In the step D, the reaction temperature of liquid phase oxidation is in the range of 120 to 240° C. and preferably in the range of 150 to 220° C. The reaction pressure is in the range of 0.0 to 3.6 MPaG, preferably in the range of 0.1 to 3.2 MPaG and more preferably in the range of 0.2 to 2.7 MPaG.

The reaction mixture obtained in step D is fed to step B and trimethyl benzoic acid and trimethyl benzaldehyde produced in step D are separated from the reaction mixture. Trimethyl benzoic acid and trimethyl benzaldehyde separated in step B are fed to step C. Herein, the process for feeding the reaction mixture of step D to step B is not limited. For example, the reaction mixture of step D may be mixed in the reaction mixture of step A or may be fed directly to each apparatus of step B including two-phase separator without being mixed.

In the oxidation reaction of steps A, C and D, an oxygen-containing gas is used. Examples of the oxygen-containing gas include air, an oxygen gas and a mixed gas of oxygen and an inert gas such as nitrogen and argon, among which air is industrially most advantageous.

As a reactor for oxidation, a stirring vessel and a babble column can be used. A stirring vessel is preferable since stirring can be sufficiently conducted in a reactor. As a reaction process, all of a batch wise, a semibatch wise and a continuous process can be applied, among which a continuous process is preferable.

The oxygen concentration in an exhaust gas from the reactor is in the range of 0.1 to 8% by volume and preferably in the range of 1 to 5% by volume. It is preferable that the reactor is equipped with a reflux condenser which condenses a large amount of solvent to be entrained in an exhaust gas and water to be produced in the oxidation reaction. The solvent and water thus condensed are usually recycled to the reactor and a portion thereof is also withdrawn outside the reaction system in order to adjust water concentration in the reactor.

(Step E)

In step E, trimethyl benzyl alcohol separated in step B is subjected to liquid phase hydrogenation reduction with molecular hydrogen, whereby durene is obtained.

In the hydrogenation reduction of trimethyl benzyl alcohol, it is preferable to use a solvent. The solvent may be the self solvent of trimethyl benzyl alcohol or other solvent. When other solvent is used, aromatic hydrocarbons and/or water is (are) preferable and durene and/or water is more preferable, among which durene is the most preferable. The amount of the solvent is in the range of 0 to 12 and preferably in the range of 2 to 6 (including the case of self solvent) as a weight ratio (SR) of solvent to the raw material for hydrogenation (trimethyl benzyl alcohol). When durene and/or water is (are) used as the solvent, it is preferable since additional separation is not necessary in the reuse of durene obtained in step E.

In the hydrogenation reduction of step E, it is preferable to use a catalyst. At least one species of heavy metal compound is preferable as the catalyst. Herein, as the heavy metal, at least one metal selected from the group rhodium, palladium, ruthenium, platinum, nickel, iron, tungsten, copper, cobalt and manganese is preferable, among which at least one metal selected from the group consisting of rhodium, ruthenium and platinum is more preferable. These metals are used as compounds such as metal oxides, organic acid salts and halogenides, among which organic acid salts such as acetic acid salts and naphthenic acid salts are preferable.

The amount of the catalyst to be used is in the range of 0.01 to 3% by weight and preferably in the range of 0.02 to 1.0% by weight as metal atom to trimethyl benzyl alcohol as a raw material for hydrogenation.

In step E, the reaction temperature for hydrogenation reduction is in the range of 20 to 230° C. and preferably in the range of 80 to 180° C. The reaction pressure is in the range of 0.1 to 10 MPaG, preferably in the range of 0.2 to 4.0 MPaG and more preferably in the range of 0.3 to 2.4 MPaG. As a reaction process, all of a batch wise, a semibatch wise and a continuous process may be applied, among which a continuous process is preferable.

Durene obtained in step E is separated and fed to step B. Herein, the process for feeding durene obtained in step E to step B is not limited. For example, durene obtained in step E may be mixed in the reaction mixture of step A or may be fed directly to each apparatus of step B including two-phase separator without being mixed.

It is preferable that at least one step in steps A, C, D and E is a continuous process.

PREFERRED EMBODIMENT OF THE INVENTION

The present invention will be described in more detail below, referring to Examples, which are not intended to limit the scope of the present invention.

EXAMPLE 1

(Step A)

Durene as a starting material at the rate of 331 g/h, trimethyl benzoic acid at the rate of 55 g/h and water as a solvent at the rate of 342 g/h were fed to a titanium autoclave of 2 L (reactor 1), equipped with a gas exhaust pipe with a reflux cooling tube, a gas injection nozzle and a stirrer. Cobalt acetate tetrahydrate salt as a catalyst was added thereto so as to maintain a cobalt concentration of 500 ppm to the solvent. The reactor interior temperature was raised in a nitrogen atmosphere. Air was introduced therein at 120° C. under 0.4 MPaG and the continuous reaction was performed in a residence time of 50 minutes.

(Step B)

The reaction mixture obtained in the above-mentioned reaction was standing to separate into an aqueous phase and an oily phase comprising durene. This oily phase was subjected to vacuum distillation under 200 torr (about 27 kPa) in a distillation column corresponding to the theoretical step of 8 steps, whereby durene was separated. Then, the oily phase separated durene is subjected to vacuum distillation under 20 torr (about 2.7 kPa) in a distillation column corresponding to the theoretical step of 15 steps, whereby each distillate comprising each of trimethyl benzoic acid, trimethyl benzaldehyde and trimethyl benzyl alcohol as a main component was separated.

(Step D)

Trimethyl benzyl alcohol separated in step B as a raw material at the rate of 200 g/h and durene at the rate of 800 g/h as a solvent were fed to a titanium autoclave of 2 L (reactor 2), equipped with a gas exhaust pipe with a reflux cooling tube, a gas injection nozzle and a stirrer. Manganese naphthenate and copper naphthenate as a catalyst were added thereto so as to maintain manganese concentration 200 ppm and copper concentration 50 ppm to the solvent. The reactor interior temperature was raised in a nitrogen atmosphere. Air was introduced therein at 170° C. under 0.4 MPaG and the continuous reaction was performed in a residence time 120 minutes.

The reaction mixture thus obtained was added to the above-mentioned oily phase comprising durene in step B.

(Step C)

Trimethyl benzoic acid at the rate of 25 g/h, trimethyl benzaldehyde at the rate of 5 g/h separated in step B as raw materials and water as a solvent at the rate of 230 g/h was fed to a zirconium autoclave of 2 L (reactor 3), equipped with a gas exhaust tube with a reflux cooling tube, a gas injection nozzle and a stirrer. Manganese bromide tetrahydrate, iron bromide and hydrogen bromide as a catalyst were added thereto so as to maintain manganese concentration 0.43% by weight, iron concentration 0.0008% by weight and bromine concentration 2.4% by weight to the solvent. The reactor interior temperature was raised in a nitrogen atmosphere. Air was introduced therein at 215° C. under 3.0 MPaG and the continuous reaction was performed in a residence of 90 minutes.

The reaction products thus obtained were analyzed. The yield of pyromellitic acid to reacted durene in all steps was 73.2 mol %. The result is shown in Table 1.

EXAMPLE 2

The experiment was performed in the same manner as in Example 1 except that the feeding rate of trimethyl benzoic acid in step A was changed to 165 g/h. The result is shown in Table 1.

EXAMPLE 3

The experiment was performed in the same manner as in Example 1 except that cobalt naphthenate in step D was used instead of manganese naphthenate. The result is shown in Table 1.

EXAMPLE 4

The experiment was performed in the same manner as in Example 1 except that the feeding rate of trimethyl benzoic acid in step A was changed to 0 g/h. The result is shown in Table 1.

EXAMPLE 5

The experiment was performed in the same manner as in Example 1 except that the feeding rate of water as a solvent in step A was changed to 0 g/h. The result is shown in Table 1.

EXAMPLE 6

The experiment was performed in the same manner as in Example 1 except that the feeding rate of durene as a solvent in step D was changed to 0 g/h. The result is shown in Table 1.

EXAMPLE 7

(Step A)

Durene as a starting material at the rate of 331 g/h, trimethyl benzoic acid at the rate of 55 g/h and water as a solvent at the rate of 342 g/h was fed to a titanium autoclave of 2 L (reactor 1), equipped with a gas exhaust pipe with a reflux cooling tube, a gas injection nozzle and a stirrer. Cobalt acetate tetrahydrate salt as a catalyst was added thereto so as to maintain a cobalt concentration of 500 ppm to the solvent. The reactor interior temperature was raised in a nitrogen atmosphere. Air was introduced therein at 120° C. under 0.4 MPaG and the continuous reaction was performed in a residence time of 50 minutes.

(Step B)

The reaction mixture obtained in the above-mentioned reaction was standing to separate into an aqueous phase and an oily phase comprising durene. This oily phase was subjected to vacuum distillation under 200 torr (about 27 kPa) in a distillation column corresponding to the theoretical step of 8 steps, whereby durene was separated. Then, the oily phase separated durene is subjected to vacuum distillation under 20 torr (about 2.7 kPa) in a distillation column corresponding to the theoretical step of 15 steps, whereby each distillate comprising each of trimethyl benzoic acid, trimethyl benzaldehyde and trimethyl benzyl alcohol as a main component was separated.

(Step E)

Trimethyl benzyl alcohol separated in step B as a raw material at the rate of 200 g/h and durene at the rate of 800 g/h as a solvent were fed to a titanium autoclave of 2 L (reactor 2), equipped with a gas exhaust pipe with a reflux cooling tube, a gas injection nozzle and a stirrer. Ruthenium black as a catalyst was added thereto so as to maintain ruthenium concentration 500 ppm to the solvent. The reactor interior temperature was raised in a hydrogen atmosphere. Hydrogen was introduced therein at 150° C. under 1.2 MPaG and the continuous reaction was performed in a residence time of 60 minutes.

Durene thus obtained was added to the above-mentioned oily phase comprising durene in step B.

(Step C)

Trimethyl benzoic acid at the rate of 25 g/h, trimethyl benzaldehyde at the rate of 5 g/h separated in step B as raw materials and water as a solvent at the rate of 230 g/h were fed to a zirconium autoclave of 2 L (reactor 3), equipped with a gas exhaust tube with a reflux cooling tube, a gas injection nozzle and a stirrer. Manganese bromide tetrahydrate, iron bromide and hydrogen bromide as a catalyst were added thereto so as to maintain manganese concentration 0.43% by weight, iron concentration 0.0008% by weight and bromine concentration 2.4% by weight to the solvent. The reactor interior temperature was raised in a nitrogen atmosphere. Air was introduced therein at 215° C. under 3.0 MPaG and the continuous reaction was performed in a residence time of 90 minutes.

The reaction products thus obtained was analyzed. The yield of pyromellitic acid to reacted durene in all steps was 72.0 mol %. The result is shown in Table 2.

EXAMPLE 8

The experiment was performed in the same manner as in Example 7 except that the feeding rate of trimethyl benzoic acid in step A was changed to 165 g/h. The result is shown in Table 2.

EXAMPLE 9

The experiment was performed in the same manner as in Example 7 except that the feeding rate of trimethyl benzoic acid in step A was changed to 0 g/h. The result is shown in Table 2.

EXAMPLE 10

The experiment was performed in the same manner as in Example 7 except that the feeding rate of water as a solvent in step A was changed to 0 g/h. The result is shown in Table 2.

COMPARATIVE EXAMPLE 1

A catalyst liquid (zirconium concentration 0.01% by weight, manganese concentration 0.37% by weight, bromine concentration 0.4% by weight and water concentration 5% by weight) mixed zirconium acetate, manganese acetate tetrahydrate, 47 wt % hydrogen bromide aqueous solution, glacial acetic acid and water at the rate of 300 g/h and durene at the rate of 73 g/h were fed to a zirconium autoclave of 2L, equipped with a gas exhaust pipe with reflux cooling tube, a gas injection nozzle and a stirrer. Air was introduced at 220° C. under 3.3 MPaG and oxidation was performed in continuous one stage in a residence time of 120 minutes. The reaction stopped immediately after starting of the reaction. The result is shown in Table 2.

COMPARATIVE EXAMPLE 2

A catalyst liquid (zirconium concentration 0.01% by weight, manganese concentration 0.37% by weight, bromine concentration 0.4% by weight and water concentration 5% by weight) mixed zirconium acetate, manganese acetate tetrahydrate, 47 wt % hydrogen bromide aqueous solution, glacial acetic acid and water at the rate of 300 g/h and durene at the rate of 73 g/h were fed to a zirconium autoclave of 2L, equipped with a gas exhaust pipe with a reflux cooling tube, a gas injection nozzle and a stirrer. Air was introduced at 220° C. under 3.3 MPaG and oxidation was performed in batch one stage in a residence time of 90 minutes. The result is shown in Table 2.

Pyromellitic acid to be obtained in the present invention is useful as a raw material for particular plasticizer, polyamide and imide.

TABLE 1

| Example | Example 1 | Example 2 | Example 3 | Example 4 | Example 5 | Example 6 |
|---|---|---|---|---|---|---|
| Step A | | | | | | |
| DRN (mol %) | 8.5 | 8.3 | 8.5 | 8.6 | 87.5 | 8.5 |
| TMBA (mol %) | 1.2 | 3.6 | 1.2 | 0.0 | 12.5 | 1.2 |
| Water (mol %) | 90.3 | 88.1 | 90.3 | 91.4 | 0.0 | 90.3 |
| Catalyst species | Co | Co | Co | Co | Co | Co |
| Step D | | | | | | |
| TMBALc (mol %) | 18.7 | 18.7 | 18.7 | 18.7 | 18.7 | 100.0 |
| DRN (mol %) | 81.3 | 81.3 | 81.3 | 81.3 | 81.3 | 0.0 |
| Catalyst species | Mn + Cu | Mn + Cu | Co + Cu | Mn + Cu | Mn + Cu | Mn +Cu |
| Step C | | | | | | |
| TMBA + TBAL (mol %) | 1.1 | 1.1 | 1.1 | 1.1 | 1.1 | 1.1 |
| Water (mol %) | 98.9 | 98.9 | 98.9 | 98.9 | 98.9 | 98.9 |
| PMA Yield (mol %) (based on reacted DRN) | 73.2 | 70.5 | 69.4 | 59.1 | 65.7 | 50.9 |

Each abbreviation in Tables 1 and 2 is follows:
DRN: durene
TMBA: trimethyl benzoic acid
TBAL: trimethyl benzaldehyde
TMBALc: trimethyl benzyl alcohol
PMA: pyromellitic acid

TABLE 2

| Example & Comp. Ex. | Example 7 | Example 8 | Example 9 | Example 10 | Comp. Ex. 1 | Comp. Ex. 2 |
|---|---|---|---|---|---|---|
| Step A | | | | | | |
| DRN (mol %) | 8.5 | 8.3 | 8.6 | 87.5 | — | — |
| TMBA (mol %) | 1.2 | 3.6 | 0.0 | 12.5 | — | — |
| Water (mol %) | 90.3 | 88.1 | 91.4 | 0.0 | — | — |
| Catalyst species | Co | Co | Co | Co | — | — |
| Step E | | | | | — | — |
| TMBALc (mol %) | 18.7 | 18.7 | 18.7 | 18.7 | — | — |
| DRN (mol %) | 81.3 | 81.3 | 81.3 | 81.3 | — | — |
| Catalyst species | Ru | Ru | Ru | Ru | — | — |
| Step C | | | | | | |
| TMBA + TBAL (mol %) | 1.1 | 1.1 | 1.1 | 1.1 | — | — |
| Water (mol %) | 98.9 | 98.9 | 98.9 | 98.9 | — | — |
| PMA Yield (mol %) (based on reacted DRN) | 72.0 | 70.3 | 58.6 | 65.1 | 0.0 | 50.6 |

What is claimed is:

1. A process for producing pyromellitic acid which comprises:

step A for oxidizing durene in the presence of trimethyl benzoic acid added to durene prior to oxidation in a solvent consisting of water, thereby obtaining a reaction mixture comprising trimethyl benzoic acid, trimethyl benzyl alcohol, trimethyl benzaldehyde, and unreacted durene, step B for separating trimethyl benzoic acid, trimethyl benzaldehyde and trimethyl benzyl alcohol from the reaction mixture obtained in step A, and step C for oxidizing trimethyl benzoic acid and/or trimethyl benzaldehyde separated in step B in a solvent consisting of water, thereby obtaining pyromellitic acid.

2. A process for producing pyromellitic acid which comprises:

step A for oxidizing durene in a solvent consisting of water, thereby obtaining a reaction mixture comprising trimethyl benzoic acid, trimethyl benzyl alcohol, trimethyl benzaldehyde, and unreacted durene, step B for separating trimethyl benzoic acid, trimethyl benzaldehyde and trimethyl benzyl alcohol from the reaction mixture obtained in step A, and step D for oxidizing trimethyl benzyl alcohol separated in step B and then feeding trimethyl benzoic acid and trimethyl benzaldehyde thus obtained by oxidation reaction to step B, and step C for oxidizing trimethyl benzoic acid and/or trimethyl benzaldehyde separated in step B in a solvent consisting of water, thereby obtaining pyromellitic acid.

3. A process for producing pyromellitic acid which comprises:

step A for oxidizing durene in a solvent consisting of water, thereby obtaining a reaction mixture comprising trimethyl benzoic acid, trimethyl benzyl alcohol, trimethyl benzaldehyde, and unreacted durene, step B for separating trimethyl benzoic acid, trimethyl benzaldehyde and trimethyl benzyl alcohol from the reaction mixture obtained in step A, and step E for performing hydrogenation reduction of trimethyl benzyl alcohol separated in step B and then feeding durene thus obtained by hydrogenation reduction to step B, and step C for oxidizing trimethyl benzoic acid and/or trimethyl benzaldehyde separated in step B in a solvent consisting of water, thereby obtaining pyromellitic acid.

4. The process according to any one of claims 2 to 3, wherein trimethyl benzoic acid is present together with durene in the oxidation reaction of step A.

5. The process according to any one of claims 1 to 3, wherein the weight ratio of the solvent to durene in step A is in the range of 0.2 to 10.

6. The process according to claim 4, wherein the amount of trimethyl benzoic acid relative to the total amount of solvent in step A is 0.1 to 40% by weight.

7. The process as in one of claims 1 to 3, wherein a cobalt compound and/or a manganese compound is/are used as a catalyst in step A and the reaction temperature is in the range of 90 to 230° C. and the reaction pressure is in the range of 0.1 to 4.0 MPaG in step A.

8. The process according to claim 7, wherein the amount of the catalyst is in the range of 0.01 to 2% by weight on a metal atom(s) in the catalyst to durene basis.

9. The process according to claim 2, wherein in step D, at least one metal compound selected from the group consisting of cobalt compound, manganese compound, and copper compound is used as a catalyst; aromatic hydrocarbons and/or water is (are) used as a solvent(s); the reaction temperature is in the range of 120 to 240° C. and the reaction pressure is in the range of 0.0 to 3.6 MPaG in step D.

10. The process according to claim 9, wherein the amount of the catalyst is in the range of 0.01 to 1% by weight on a metal atom(s) in the catalyst to trimethyl benzyl alcohol basis.

11. The process according to claim 2, wherein the weight ratio of the solvent(s) to trimethyl benzyl alcohol in step D is in the range of 1 to 12.

12. The process according to claim 3, wherein at least one metal compound selected from the group consisting of rhodium compound, palladium compound, ruthenium compound, platinum compound, nickel compound, iron compound, tungsten compound, copper compound, cobalt compound, and manganese is used as a catalyst in step E; the reaction temperature is in the range of 20 to 230° C. and the reaction pressure is in the range of 0.1 to 10 MPaG in step E.

13. The process according to claim 12, wherein the amount of the catalyst is in the range of 0.01 to 3% by weight on a metal atom(s) in the catalyst to trimethyl benzyl alcohol basis.

14. The process according to claim 12, wherein the hydrogenation reduction is performed using self solvent of trimethyl benzyl alcohol or aromatic hydrocarbons and/or water as a solvent(s) in step E and the weight ratio of the solvent(s) to trimethyl benzyl alcohol is in the range of 0 to 12.

15. The process according to any one of claims 1 to 3, wherein at least one metal compound selected from the group consisting of cobalt compound, manganese compound and iron compound and a bromine compound are used as a catalyst in step C.

16. The process according to claim 15, wherein the total amount of metal(s) in the catalyst to be used is in the range of 0.01 to 1% by weight on a metal atom(s) in the catalyst to solvent basis.

17. The process according to claim 15, wherein the total bromine concentration in the reaction system of step C is in the range of 0.1 to 4.0% by weight on a bromine atom to solvent basis.

18. The process according to claim 1, wherein at least one step in steps A and C is a continuous process.

19. The process according to claim 2, wherein at least one step in steps A, C, and D is a continuous process.

20. The process according to claim 3, wherein at least one step in steps A, C, and E is a continuous process.

21. The process according to any one of claims 1 to 3, wherein in step B, the reaction mixture is separated into each of an oily phase containing mainly unreacted durene, trimethyl benzoic acid, trimethyl benzyl alcohol and an aqueous phase, and then the oily phase thus separated is subjected to vacuum distillation, whereby each distillate comprising each of unreacted durene, trimethyl benzoic acid, trimethyl benzaldehyde and trimethyl benzyl alcohol as main component is separately obtained.

22. The process according to claim 21, wherein unreacted durene separated in step B is recycled to step A, or is fed to step D to use as a solvent.

* * * * *